United States Patent [19]

Schrell et al.

[11] Patent Number: 5,695,529
[45] Date of Patent: Dec. 9, 1997

[54] LIQUID FORMULATION OF N-(2-SULFATOETHYL)PIPERAZINE SULFATE

[75] Inventors: Andreas Schrell, Frankfurt; Michael Meier, Liederbach; Heinz Georg Kautz, Bierstein, all of Germany

[73] Assignee: Hoechst Aktiengesellschaft, Frankfurt, Germany

[21] Appl. No.: 770,291

[22] Filed: Dec. 20, 1996

[30] Foreign Application Priority Data

Dec. 20, 1995 [DE] Germany .................. 195 47 649.2

[51] Int. Cl.⁶ .................................................. D06M 13/322
[52] U.S. Cl. ............................ 8/189; 8/930; 252/8.86
[58] Field of Search ........................ 8/189, 493, 930; 544/398, 401; 252/8.86

[56] References Cited

U.S. PATENT DOCUMENTS

| 5,507,804 | 4/1996 | Llanos | 623/11 |
| 5,542,954 | 8/1996 | Schrell et al. | 8/532 |
| 5,563,271 | 10/1996 | Meier et al. | 544/398 |
| 5,575,821 | 11/1996 | Schrell et al. | 8/493 |

FOREIGN PATENT DOCUMENTS

| 9304773 | 7/1994 | Brazil . |
| 1097008 | 1/1995 | China . |
| 0546476 | 6/1993 | European Pat. Off. . |
| 601351 | 6/1994 | European Pat. Off. . |
| 4402210 | 7/1995 | Germany . |
| 07002813 | 1/1995 | Japan . |

*Primary Examiner*—Jose G. Dees
*Assistant Examiner*—M. Cebulak
*Attorney, Agent, or Firm*—Connolly & Hutz

[57] ABSTRACT

A 5% strength by weight to saturated aqueous solution of N-(2-sulfatoethyl)piperazine sulfate, having a pH of between 4 and 0, can be used to modify fiber material.

13 Claims, No Drawings

LIQUID FORMULATION OF N-(2-SULFATOETHYL)PIPERAZINE SULFATE

The present description relates to an aqueous liquid formulation of N-(2-sulfatoethyl)piperazine sulfate and to its use for modifying fiber material.

N-(2-Sulfatoethyl)piperazine sulfate is known from U.S. Pat. No. 5,563,271 and can be employed as a means of pretreating and modifying fiber materials such as synthetic polyamide or polyurethane fiber materials, wool, silk or cellulose fiber materials, for subsequent dyeing with anionic dyes, especially reactive dyes (U.S. Pat. No. 5,507,804 and U.S. Pat. No. 5,575,821). The method of preparing this compound described in U.S. Pat. No. 5,563,271 requires large quantities of ethanol, making said preparation technique highly disadvantageous from an ecological and economic standpoint. Moreover, it is accompanied by the formation of unwanted byproducts with a severe negative effect on the industrial application.

There was therefore an urgent need for a preparation method which avoids these disadvantages. This objective has surprisingly been achieved by an aqueous alcohol-free liquid formulation of this compound.

The invention provides a 5% strength by weight to saturated aqueous solution of N-(2-sulfatoethyl)piperazine sulfate having a pH of between 4 and 0. Economically speaking, it is expedient to formulate for an N-(2-sulfatoethyl)piperazine sulfate content which is as high as possible, i.e. at or near the saturation point.

Preference is therefore given to an aqueous solution having a content of from 25 to 65% by weight, preferably from 30 to 60% by weight, particularly preferably from 35 to 54% by weight, and with special preference from 40 to 52% by weight, of N-(2-sulfatoethyl)piperazine sulfate. In order to avoid precipitation at low temperatures, it is advantageous to keep somewhat below the room-temperature saturation point.

So that N-(2-sulfatoethyl)piperazine sulfate remains stable in aqueous solution even for prolonged periods, it is advantageous for the pH to be low, in particular from 0 to 3, especially from 0.1 to 2, and, with very particular preference, from 0.3 to 1.

The invention also provides a process for preparing the novel solution, which comprises reacting N-(2-hydroxyethyl)piperazine with a sulfonating agent consisting of from 70 to 100% strength by weight sulfuric acid or $SO_3$ or oleum or chlorosulfonic acid, or a mixture thereof, especially from 90 to 98% strength by weight sulfuric acid, and introducing the reaction mixture into an amount of water sufficient, with or without the addition of an inorganic base such as an alkali metal hydroxide or alkali metal carbonate, to give the novel aqueous solution.

N-(2-Hydroxyethyl)piperazine and its preparation are part of general knowledge, and the product is available commercially in a concentration, for example, of from 95 to 98% by weight.

It is advantageous to conduct the reaction at temperatures from 120° to 220° C., preferably from 140° to 180° C., such that the water of reaction that is formed is removed. It is also advantageous to carry out the reaction at reduced pressure, for example at from 0.1 to 200 mbar. Once the reaction is over, the viscous reaction mixture can be introduced directly into water.

The sulfonating agent is expediently employed in an amount of from 1.6 to 2.2 parts by weight, preferably from 1.8 to 2.0 parts by weight, per part by weight of N-(2-hydroxyethyl)piperazine. It is also possible to use larger amounts of said sulfonating agents, but this does not give any advantages in terms of quality and results merely in the need to neutralize larger amounts of acid in the course of subsequent use.

In a particularly advantageous embodiment, N-(2-hydroxyethyl)piperazine is added to an initial charge of 96% strength by weight sulfuric acid at a rate such that if possible a temperature of 150° C. is not exceeded. Subsequently, the reaction vessel is evacuated slowly and the corresponding water of reaction is distilled off at about 150° C. When the reaction time is over, the still hot sulfonation mixture is run into an ice/water mixture and its pH is adjusted to 0.5 with sodium hydroxide solution. The result of this is a solution of sodium sulfate and the desired substance in water, which apart from small amounts of starting substance comprises exclusively N-(2-sulfatoethyl)piperazine sulfate. The byproducts formed in the synthesis according to U.S. Pat. No. 5,563,271 are not present.

The solution obtained after partial neutralization of the sulfuric acid can be used directly for modifying cellulose-containing fiber materials, as described in U.S. Pat. No. 5,542,954.

In the examples below, percentages are by weight.

EXAMPLE 360 g of 96% strength sulfuric acid are placed in a 750 ml flask fitted with stirrer, dropping funnel, thermometer and distillation bridge, and 195.1 g (1.5 mol) of 98% pure N-(2-hydroxyethyl)piperazine are added over the course of about 20 minutes at a rate such that the temperature does not climb above 150° C. During this addition, first a mist and then water of condensation is formed. The vessel is subsequently evacuated to 10 mbar over 30 minutes and the mixture is then stirred at 150° C. for 5 hours. 39.8 g of water are condensed in an acetone/carbon dioxide cold trap. The reaction mixture is transferred while still hot to a dropping funnel and is metered into 210 g of water at a rate such that the temperature does not exceed 30° C. Then a pH of 0.5 is established using 143.1 g of 50% strength sodium hydroxide solution. When this addition is over, the mixture is stirred at 25° C. for 30 minutes and filtered to remove any undissolved fraction. The filter cake is washed with 30 g of water. 0.1 g of filter residue and 898.8 g=564 ml of N-(2-sulfatoethyl)piperazine sulfate solution, as a light brown liquid, are obtained. The content by titration is about 51%, corresponding to 457.9 g (1.49 mol) of N-(2-sulfatoethyl)piperazine sulfate, calculated on a 100% basis, and to a yield of 99% of theory.

USE EXAMPLE

A cotton interlock tube is immersed at 100° C., in a continuous procedure, into a bath containing 1%, based on the amount of liquid, of 50% strength sodium hydroxide solution and 1%, based on the amount of liquid, of 35% strength hydrogen peroxide solution. The goods are left in the bath for 10 minutes and then passed through a squeeze roll unit to leave a liquor add-on about 80%. The material is subsequently passed through a wetting trough with a multiple squeeze roll unit, containing a solution of which each liter contains 210 g of the 50% strength aqueous N-(2-sulfatoethyl)piperazine sulfate from the example above and 210 ml of 50% strength sodium hydroxide solution. In this procedure, the material is impregnated with a liquor add-on of 110%. The rope of goods is then treated further by being passed into a J box where it remains for 30 minutes at a temperature of between 95° and 98° C. It is then rinsed thoroughly, freed from dissolved dirt particles and excess alkali, and adjusted to a residual moisture content of 100%. The still wet material can subsequently be dyed directly by an exhaust method in a jet dyeing machine, for which purpose 10,000 parts of water are added to 1000 parts of the material.

Subsequently, 20 parts of a dye of the formula

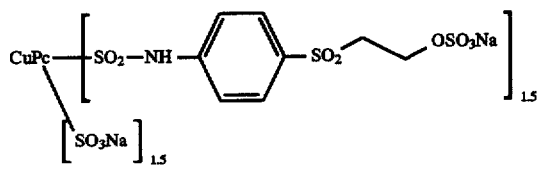

which is known from Example 2 of DE-A1-1179317 are metered in over a period of 10 minutes. The bath is heated to 80° C. and the material is left at this temperature for 45 minutes. The bath is then cooled to 60° C., the residual liquor is drained off, and the material is treated by customary methods. After it has been dried, a strong turquoise dyeing is obtained with good in-service fastness properties.

We claim:

1. A 5% strength by weight to saturated aqueous alcohol-free solution of N-(2-sulfatoethyl)piperazine sulfate, having a pH of between 4 and 0.

2. An aqueous solution as claimed in claim 1, wherein the content of N-(2-sulfatoethyl)piperazine sulfate is from 25 to 65% by weight.

3. An aqueous solution as claimed in claim 1, wherein the content of N-(2-sulfatoethyl)piperazine sulfate is from 40 to 52% by weight.

4. An aqueous solution as claimed in claim 1, wherein the pH of the solution is between 3 and 0.

5. An aqueous solution as claimed in claim 1, wherein the pH of the solution is between 1 and 0.3.

6. A process for preparing an aqueous solution as claimed in claim 1, which comprises reacting N-(2-hydroxyethyl)piperazine with a sulfonating agent comprising from 70 to 100% strength by weight sulfuric acid or oleum or sulfur trioxide or chlorosulfonic acid, or a mixture thereof, and introducing the resulting reaction mixture into an amount of water which is sufficient, with or without the addition of an inorganic base, to give said aqueous solution.

7. The process as claimed in claim 6, wherein from 90 to 98% strength by weight sulfuric acid is employed.

8. The process as claimed in claim 6, wherein the sulfonating agent is employed in an amount of from 1.6 to 2.2 parts by weight, per part by weight of N-(2-hydroxyethyl)piperazine.

9. The process as claimed in claim 6, wherein the sulfonating agent is employed in an amount of from 1.8 to 2.0 parts by weight, per part by weight of N-(2-hydroxyethyl)piperazine.

10. The process as claimed in claim 6, wherein the reaction is carried out at a temperature between 120° and 220° C.

11. The process as claimed in claim 6, wherein the reaction is carried out at a temperature between 140° and 180° C.

12. The process as claimed in claim 6, wherein the reaction is carried out under reduced pressure.

13. A method for modifying a cellulose-containing fiber material comprising the step of contacting said fiber material with an aqueous solution as claimed in claim 1.

* * * * *